United States Patent
Zicker et al.

(10) Patent No.: US 8,592,479 B2
(45) Date of Patent: *Nov. 26, 2013

(54) ANTIOXIDANT-CONTAINING FOOD COMPOSITION FOR USE IN ENHANCING ANTIVIRAL IMMUNITY IN COMPANION ANIMALS

(75) Inventors: Steven C. Zicker, Lawrence, KS (US); Jeffrey A. Brockman, Lawrence, KS (US); Nolan Zebulon Frantz, Topeka, KS (US)

(73) Assignee: Hill's Pet Nutrition, Inc., Topeka, KS (US)

( * ) Notice: Subject to any disclaimer, the term of this patent is extended or adjusted under 35 U.S.C. 154(b) by 558 days.

This patent is subject to a terminal disclaimer.

(21) Appl. No.: 12/336,024

(22) Filed: Dec. 16, 2008

(65) Prior Publication Data

US 2009/0149529 A1    Jun. 11, 2009

Related U.S. Application Data

(63) Continuation-in-part of application No. 11/154,210, filed on Jun. 16, 2005, which is a continuation of application No. 09/978,132, filed on Oct. 16, 2001, now Pat. No. 6,914,071, which is a continuation-in-part of application No. 09/922,660, filed on Aug. 6, 2001, now abandoned.

(60) Provisional application No. 60/253,448, filed on Nov. 28, 2000, provisional application No. 60/244,504, filed on Oct. 31, 2000.

(51) Int. Cl.
*A23K 1/00* (2006.01)

(52) U.S. Cl.
USPC ............................ 514/440; 426/635; 426/805

(58) Field of Classification Search
USPC .................................................. 426/635, 805
See application file for complete search history.

(56) References Cited

U.S. PATENT DOCUMENTS

| | | | | |
|---|---|---|---|---|
| 5,006,361 | A | * | 4/1991 | Cox ................................ 426/601 |
| 5,030,458 | A | | 7/1991 | Shug et al. |
| 5,292,538 | A | * | 3/1994 | Paul et al. ......................... 426/74 |
| 5,883,083 | A | | 3/1999 | Harless |
| 5,916,912 | A | | 6/1999 | Ames et al. |
| 5,937,790 | A | * | 8/1999 | Ito et al. .......................... 119/174 |
| 6,080,788 | A | | 6/2000 | Sole et al. |
| 6,232,346 | B1 | | 5/2001 | Sole et al. |
| 6,335,361 | B1 | | 1/2002 | Hamilton |
| 6,914,071 | B2 | * | 7/2005 | Zicker et al. ................... 514/440 |
| 2001/0043983 | A1 | | 11/2001 | Hamilton |

FOREIGN PATENT DOCUMENTS

| | | |
|---|---|---|
| CA | 2285490 A | 4/2001 |
| EP | 1118332 | 7/2001 |
| WO | 9402036 A1 | 2/1994 |
| WO | 9843617 A2 | 10/1998 |
| WO | 0044375 A1 | 3/2000 |
| WO | 0158271 A | 8/2001 |
| WO | WO2006/058248 | 6/2006 |
| WO | WO2006/069241 | 6/2006 |
| WO | WO2006/074089 | 7/2006 |
| WO | WO2007/094669 | 8/2007 |
| WO | WO2007/149815 | 12/2007 |
| ZA | 9605149 A | 3/1997 |

OTHER PUBLICATIONS

Packer et al. Free Radical Biology & Medicine, vol. 19, No. 2, pp. 227-250, 1995.*
Information Network Villiage. Specialties (Agricultural Produce). http://www.invil.org/english/speciality/vegetable/potato/contents.jsp?con_no=602519&page_no=1.*
Information Network Villiage. Specialties (Agricultural Produce). http://www.invil.org/english/specialty/vegetable/potato/contents.jsp?con_no=602519&page_no=1. Copyright 2002. Retrieved Sep. 30, 2011.*
Branam, J. Edward, "Dietary Managment of Geriatric Dogs and Cats," Veterinary Technician (1987) 8:10 pp. 501-503.
Kolb, E. et al. Zum Bedarf an Vitaminen Und an Ascorbinasaeure . . . Konstanz, DE (1997) 52:12 pp. 728-733, English Abstract Only.
Caprioli, A. et al. Age-Dependent Deficits in Radial Maze Performance in the Rat: Effect of Chronic Treatment With Acetyl-LCarnitine; Pro. Neuro-Psychopharmacol & Biol. Psychiat (1990) 14 pp. 359-369.
Crayhon, R. Total Health (1998) 20:2 pp. 27-35.
Emmons, B "Antioxidants to the rescue" South Bend Tribune (1999) South Bend IN.
Sastre, Juan et al., "A Ginko Biloba Extract (EGb 761) Prevents Mitochondrial Aging By Protecting Against Oxidative Stress," Free Radical Biology & Medicin (1998) pp. 298-304, 24:2.
Epinions.com (http://www.epinions.com/review/Hill_s_Science_Diet_Canine_Senior/pets-review-7CC1-752D32C-39779C59-prod4) (Jul. 2000).
Dzanis David (J Nutr. Dec. 1994; 124 (12Suppl):2535S-2539S).
McGahon, Bernadette M, "Age-related changes in LTP and antioxidant defenses are reversed by an -lipoic acid enriched diet," Nuerobiology of Aging (1999) pp. 655-664 20.

* cited by examiner

*Primary Examiner* — Jeffrey S. Lundgren
*Assistant Examiner* — Chris Simmons
(74) *Attorney, Agent, or Firm* — Thomas M. Hunter

(57) ABSTRACT

The invention encompasses compositions for enhancing the ability of a companion animal to resist and/or overcome viral infections. The compositions of the invention include an amount of lipoic acid that is effective in enhancing the antiviral immunity of a companion animal.

7 Claims, No Drawings

ANTIOXIDANT-CONTAINING FOOD COMPOSITION FOR USE IN ENHANCING ANTIVIRAL IMMUNITY IN COMPANION ANIMALS

CROSS REFERENCE TO RELATED APPLICATIONS

This application is a continuation-in-part of pending application Ser. No. 11/154,210, filed Jun. 16, 2005, which is a continuation of application Ser. No. 09/978,132 filed Oct. 16, 2001, which issued as U.S. Pat. No. 6,914,071, which is a continuation-in-part of application Ser. No. 09/922,660 filed Aug. 6, 2001, which claims benefit of Provisional Application Ser. No. 60/253,448 filed Nov. 28, 2000 and Provisional Application Ser. No. 60/244,504, filed Oct. 31, 2000, each of which is incorporated herein by reference in its entirety.

FIELD OF THE INVENTION

The invention encompasses compositions for enhancing the ability of a companion animal to resist and/or overcome viral infections. The compositions of the invention include an amount of lipoic acid that is effective in enhancing the antiviral immunity of a companion animal.

BACKGROUND OF THE INVENTION

Companion animals such as dogs and cats seem to suffer from aging problems. Some of these are manifested in commonplace sayings. One of these is "You can't teach an old dog new tricks." This saying arises from the observation that as dogs age, their mental capacity seems to diminish as well as physical abilities. Mental activities associated with thinking, learning and memory seem to be lessened (Cummings, B. J., Head. E., Ruehl. W., Milgram. N. W. & Cotman, C. W. (1996): The canine as an animal model of aging and dementia. Neurobiology of Aging 17:259-268). Additionally. behavioral change can be manifested in the aging animals in association with the changing mental capacity. Many causes have been assigned to this lessening of capacity.

These losses in capacity are generally observed in aged canines and felines. Dogs of seven years or older and felines of seven years or older are considered aged and can experience this problem.

The presence of significant levels of at least one antioxidant in the diet of an adult companion pet or fed to a pet outside his diet can inhibit the onset of deterioration of the mental capacity of the aged companion pet and/or maintain the mental capacity of the adult companion pet further into the aged years.

SUMMARY OF THE INVENTION

In accordance with the invention, there is a companion pet diet meeting ordinary nutritional requirements of an adult pet and further comprising a sufficient amount of an antioxidant or mixture thereof to inhibit the onset of deterioration of the mental capacity of said companion pet in its aged years.

Another embodiment encompasses a method for inhibiting the deterioration of the mental capacity of an aged companion pet, which comprises feeding said pet in his adult years an antioxidant or mixture thereof at sufficient levels to accomplish this inhibition.

Another embodiment encompasses a companion adult pet diet meeting ordinary nutritional requirements of an adult companion pet and further comprising an antioxidant selected from the group consisting of Vitamin E, vitamin C, alpha-lipoic acid, L-carnitine and any mixtures thereof in quantities sufficient to inhibit the deterioration of the mental capacity of said pet in its aged years.

Another embodiment of the invention encompasses methods for increasing the mental capacity of an aged companion pet, which comprises feeding the pet in its adult years an amount of an antioxidant or mixture thereof sufficient to increase the mental capacity.

Another embodiment encompasses methods for increasing the mental capacity of an adult companion pet which comprises feeding the pet an amount of an antioxidant or mixture thereof sufficient to increase the mental capacity of said pet.

Another embodiment encompasses pet food compositions including an amount of one or more antioxidants, for example, lipoic acid, effective to enhance antiviral activity in a companion animal.

DETAILED DESCRIPTION OF THE INVENTION

General Description

The invention encompasses pet food compositions including an amount of lipoic acid effective amount to enhance antiviral activity in a companion animal. In certain embodiments, the effective amount of lipoic acid to enhance antiviral activity in a companion animal is at least about 25 ppm.

In certain embodiments, the effective amount is at least about 50 ppm.

In certain embodiments, the effective amount is at least about 100 ppm.

In certain embodiments, the effective amount is about 100 ppm to about 600 ppm.

In certain embodiments, the effective amount is about 100 ppm to about 200 ppm.

In certain embodiments, the companion animal is a dog.

In certain embodiments, the companion animal is a cat.

In certain embodiments, the effective amount is effective to enhance innate antiviral activity in a companion animal.

In certain embodiments, the pet food composition comprising lipoic acid is administered at least 15 days.

In certain embodiments, the pet food composition comprising lipoic acid is administered at least 30 days.

In certain embodiments, the pet food composition comprising lipoic acid is administered at least 45 days.

In certain embodiments, the pet food composition comprising lipoic acid is administered daily.

The diet fed to the adult companion pet, for example canine and feline, is the standard normal diet fed to an animal of that age. Below is a typical diet for a canine of 1 to 6 years of age.

TABLE 1

| Component | Target |
|---|---|
| Protein (% of dry matter) | 23 |
| Fat (% of dry matter) | 15 |
| Phosphorus (% of dry matter) | 0.6 |
| Sodium (% of dry matter) | 0.3 |

Adding significant quantities of an antioxidant or mixture thereof to the companion adult pet diet can bring about delay of the onset of demonstrative changes in the behavior, particularly the deterioration of mental capacity, as specifically shown by problem-solving capacity, in an aged pet. The addition of one or more antioxidants to the companion adult pet diet can also bring about enhancement of antiviral activity in companion animals. The term, adult, is intended to mean, in general, a canine of at least 1 to 6 years and a feline of at least 1 to 6 years. An aged dog or cat is 7 years and above.

The loss of mental capacity for canines and felines has been observed for a number of years. This loss of mental capacity is manifested in numerous ways. For a canine, for example, it can be manifested as disorientation, house soiling, altered sleep-wake patterns, decreased or altered interaction with humans and other pets, and inability to learn and concentrate. These conditions can be manifested in felines as well. Alzheimer's, as exhibited in man, is not found in canines and felines.

Many theories have been advanced for this loss in mental capacity. To date, the inventors are unaware of any dietary course of action, which inhibits this loss of mental capacity or can actually bring about a positive change in mental capacity as measured by an objective parameter in dogs and cats.

The inventors have succeeded in accomplishing delaying the onset of this deterioration. By using the diet of their invention in adult companion pets it can be shown that aged pets' mental capacity can be maintained for a longer period of time. Essentially the deterioration of mental capacity can be stopped or delayed. Memory and learning ability can be improved. Overall mental alertness can be enhanced. Age related cognitive decline could be slowed. With respect to Cognitive Dysfunction Syndrome its progress can be slowed in aged dogs and clinical signs associated with this syndrome can be controlled. Prophylaxis where appropriate and pets in need of these components are the target group.

The inventors have also surprisingly found that the addition of one or more antioxidants, for example lipoic acid, is useful in enhancing the innate antiviral immune function in companion animals, for example, dogs and cats. As used herein, the term "enhance" or "enhancing" when referring to antiviral immune function refers to the ability of a companion animals to have an increased immune response to an antigen and thereby be more resistant to infection or clear viral infections from the system of the companion animal faster. Accordingly, a companion animal, for example, a dog, eating a pet food containing an antioxidant, for example, lipoic acid will be more resistant to and will clear viral infections faster than an animal not consuming antioxidants.

The component in the diet which accomplishes this is an antioxidant or mixture thereof. An antioxidant is a material that quenches a free radical. Examples of such materials include foods such as ginkgo biloba, citrus pulp, grape pomace, tomato pomace, carrot and spinach, all preferably dried, as well as various other materials such as beta-carotene, selenium, coenzyme Q10 (ubiquinone), lutein, tocotrienols, soy isoflavones, S-adenosylmethionine, gluthathione, taurine, N-acetylcysteine, vitamin E, vitamin C, alpha-lipoic acid, L-carnitine and the like. Vitamin E can be administered as a tocopherol or a mixture of tocopherols and various derivatives thereof such as esters like vitamin E acetate, succitnate, palmitate, and the like. The alpha form is preferable but beta, gamma and delta forms can be included. The D form is preferable but racemic mixtures are acceptable. The forms and derivatives will function in a Vitamin E like activity after ingestion by the pet. Vitamin C can be administered in this diet as ascorbic acid and its various derivatives thereof such as calcium phosphate salts, cholesteryl salt, 2-monophosphate, and the like, which will function in a vitamin C like activity after ingesting by the pet. They can be in any from such as liquid, semisolid, solid and heat stable form. Alpha-lipoic acid can be administered into the diet as alpha-lipoic acid or as a lipoate derivative as in U.S. Pat. No. 5,621,117, racemic mixtures, salts, esters or amides thereof, L-carnitine can be administered in the diet and various derivatives of carnitine such as the salts such as the hydrochloride, furmarate and succinates, as well as acetylated carnitine and the like, can be used.

The quantities administered in the diet, all as wt % (dry matter basis) of the diet, are calculated as the active material, per se, that is measured as free material. The maximum amounts employed should not bring about toxicity.

At least about 100 ppm or at least about 150 ppm of vitamin E can be used. In certain embodiments, the range of about 500 to about 1,000 ppm can be employed. Although not necessary a maximum of about 2,000 ppm or about 1,500 ppm is generally not exceeded.

With respect to vitamin C at least about 50 ppm is used, desirably at least about 75 ppm and more desirably at least about 100 ppm. A nontoxic maximum can be employed.

The quantity of lipoic acid can vary from at least about 25 ppm, desirably at least about 50 ppm, more desirably about 100 ppm. In various embodiments, the range of lipoic acid that can be administered dogs is about 150 ppm to about 4500 ppm. In various embodiments, the range of lipoic acid that can be administered cats is about 65 ppm to about 2600 ppm. Maximum quantities can vary from about 100 ppm to 600 ppm or to an amount which remains nontoxic to the pet. In certain embodiments, a range is from about 100 ppm to about 200 ppm.

For L-carnitine about 50 ppm, desirably about 200 ppm, more desirably about 300 ppm for canines are a useful minimum. For felines, slightly higher minimums of L-carnitine can be employed such as about 100 ppm, 200 ppm, and 500 ppm. A nontoxic maximum quantity can be employed, for example, less than about 5,000 ppm. For canines, lower quantities can be employed, for example, less than about 5,000 ppm. For canines a preferred range is about 200 ppm to about 400 ppm. For felines a preferred range is about 400 ppm to about 600 ppm.

Beta-carotene at about 1-15 ppm can be employed.

Selenium at about 0.1 up to about 5 ppm can be employed.

Lutein: at least about 5 pm can be employed.

Tocotrienols: at least about 25 ppm can be employed.

Coenzyme Q10: at least about 25 ppm can be employed.

S-adenosylmethionine: at least about 50 ppm can be employed.

Taurine: at least about 1000 ppm can be employed.

Soy isoflavones: at least about 25 ppm can be used.

N-acetylcysteine: at least about 50 ppm can be used.

Glutathione: at least about 50 ppm can be used.

Gingko biloba: at least 50 ppm of extract can be used.

The following are raw ingredients that are high in ORAC (Oxygen radical absorbing capacity) content: Spinach pomace, Tomato pomace, Citrus pulp, Grape pomace, Carrot granules, Broccoli, Green tea, Ginkgo biloba, and Corn gluten meal. When added to the diet as 1% inclusions (for a total of 5% substitution for a low ORAC ingredient such as corn) they increased the ORAC content of the overall diet and increased the ORAC content of the plasma of the animals which ate the diet containing these components. Preferably, any ingredient with an ORAC content >25.mu.mole of Trolox equivalents per gram of dry matter could be used if added at 1% in combination with four other 1% ingredients for a total of 5% addition to the diet.

Example 1

Seventeen adult beagle dogs 2-4 years of age (control n=8, antioxidant-enriched n=9) were randomly placed into a control or enriched diet group. The control diet contained 59 ppm vitamin E and <32 ppm vitamin C. The test diet had 900 ppm vitamin E and 121 ppm vitamin C. 260 ppm L-carnitine and 135 ppm alpha-lipoic acid. Approximately 1 month after starting the diet, the first problem-solving task given to dogs was a landmark discrimination learning task, which is a test of spatial attention (Milgram, N. W., Adams. B., Callahan, H., Head. E., Mackey. B., Thirlwell, C. & Cotman, C. W. (1999): Landmark discrimination learning in the dog. Leaning & Memory, 6:54-61).

Landmark discrimination learning requires subjects to select a particular object based on proximity to an object. The initial learning, however, is based on the dogs' ability to learn an object discrimination task. We have previously found that the effects of age on discrimination learning depend on task difficulty.

The adult dogs on the enriched diet made fewer errors than the adult dogs on the control food when learning the landmark 0 test (control mean=31.1, enriched mean=15.1). The adult dogs proceeded on to landmark 1 and 2 testing, where the landmark is moved further away from the positive well. Adult dogs on enriched diet learned landmark 0-2 with less errors than those on the control (number of mean errors landmark 0+1+2 (control)=132.9; number of mean errors landmark 0+1+2 (dogs on enriched diet)=87.1).

Example 2

30 adult, random source, dogs were utilized for this study. Dogs were at least 10 months of age, not pregnant, not lactating and of reasonable body weight prior to start of test. Animals were randomized into 5 groups for dietary treatment with 3 males and 3 females per each group.

All dogs were fed a control food (0 ppm DL-alpha-lipoic acid added) that met or exceeded all recommendations for nutrients as proposed by the American Association of Feed Control Officials (AAFCO 2000) during a 2 week prefeeding period (Table 1). Following the prefeeding period dogs were randomized into 5 treatment groups with one of the following DL-alpha-lipoic acid target inclusions (dry matter basis): 0 ppm, 150 ppm, 1,500 ppm, 3,000 ppm, 4,500 ppm. In all diets, control and alpha-lipoic acid, vitamin E was added and was present at a level of 600-1000 International Units, and vitamin C was added at levels of 100-200 ppm.

Test foods were the sole source of nutrients except for water. Fresh water was provided ad libitum. After dogs were selected and initial body weights taken, a food dose was calculated for each dog based on the expected ME of the food. Initial food dose calculations were based on the maintenance energy requirement (MER) for the dog modified by a factor to account for normal activity as calculated by the following formula:

$$MER(\text{kcal/day}) = 1.6 \times RER(\text{Resting Energy Requirement})$$

where: RER (kcal/day)=70.times.body weight (kg)$^{0.75}$.

Dogs were weighed weekly and had food doses adjusted as needed in order to feed enough food to maintain their optimal body weight. Optimal body weight was determined to be 3 on a 5 point scale. If a dog (lid not maintain body weight within −10% of initial body weight, after adjustment of food dose, it was removed from the study. All measures of body weight and food intake were recorded.

Samples were ground and 0.100.+−.0.001 g of sample was extracted twice into 5.0 ml phosphate buffer (10 mM $Na_2HPO_4$, 2 mM ethylenediaminetetraacetic acid (EDTA), 0.9% NaCl. pH 7.4), 250 µL of extract was placed into a 5 ml glass centrifuge tube with a Teflon lined cap. 15 µL EDTA solution (100 mM EDTA adjusted to pH 7.8 with .about.1M NaOH) and 50 .mu.l freshly prepared 5 mM dithioerythritol (DTE) were added. The solutions were vortexed and incubated at room temperature for 5 minutes. Then 10 .mu.l of 1M $H_3PO_4$ and 2.0 ml diethyl ether were added. The tubes were capped, vortexed, and centrifuged at 1500.times.g for 3 minutes at room temperature. The ether layer was transferred to a separate 5 ml glass centrifuge tube, while the aqueous layer was extracted twice more with 1.5 ml ether. All extractions from the same sample were combined. The extracts are then dried in a nitrogen evaporator in a water bath at room temperature. At this point, the samples were capped and frozen overnight.

The dried extracts were then thawed and reconstituted with 70 .mu.l SDS/EDTA solution (0.11% sodium dodecyl sulfate (SDS), 15 mM EDTA. 0.9% NaCl) and 5 µL freshly prepared 1 mM DTE. 50 µL of freshly prepared $NaBH_4$ was then added to each tube. The tubes were vortexed and incubated at room temperature for 10 minutes. After 10 minutes, the samples were frozen at −70° C. Before the solutions were thawed 20 µL 2 M HCl was added. After the solutions were thawed. 800 µL 100 mM $NH_4HCO_3$ was added. The solutions are vortexed and 5 .mu.l of 100 mM monobromiiobimane in acetonitrile solution (mBBr) was added. The solutions were then incubated in the dark for 90 minutes at room temperature.

Excess mBBr and the DTE derivative were removed from the samples after incubation by extraction with 1.5 ml dichloromethane. The aqueous layer was placed on the HPLC. The lipoic acid was separated using a mobile phase that consisted of 30% acetonitrile, 1% acetic acid, adjusted to pH 3.95 with about 2 M $NH_4OH$ and was pumped at a flow rate of 1.0 mL/min with an isocratic clution for 15 minutes per injection. This preparation assumes that the density of the extruded food is equal to 1 g/ml.

Blood was collected aseptically for complete blood count and blood biochemistry analysis 2 weeks prior to start, and again at 0, 28, 56, 84, 112, 140 and 168 days of the study. In additions 15 ml of whole blood was collected for isolation of lymphocytes at days 0, 28 and 84 of the dietary intervention.

Heparinized whole blood was layered onto a 50 ml Accuspin conical centrifuge tube (Sigma Chemical) and an equal volume of phosphate buffered saline (PBS) was added. Samples were centrifuged at 700.times.g for 30 minutes without brake. The monocyte layer was harvested, transferred to a 15 ml conical centrifuge tube, resuspended in 1-3 ml of PBS, and centrifuged as before (first wash). A second wash was performed as the first wash. Finally, cells were harvested and suspended in perchloric acid (10% w/v) and frozen at 70.degree. C. until analysis.

Samples were transferred from −70° C. freezer into a cooler with dry ice in it. Vials were centrifuged at 12,000 rpm for 5 minutes in a refrigerated centrifuge. An aliquot of supernatant for glutathione (GSH) analysis was transferred to a conical test tube.

Derivatization of the acid soluble extracts was by the method of Reed and coworkers (Fariss et al) as modified by Jones (Jones et al).

Briefly, 150 µL extract or external standards were added into a 1.5 ml eppendorf tube followed by addition of 20 µL .gamma.-glu-glu internal standard and 50 µL 1AA added followed by mixing. The solution was adjusted to pH about 10 (purple color) by using KOH—$KHCO_3$ working solution. Solutions were incubated 1 hr under room temperature in the dark. Sanger's reagent was added at the same volume as of the total volume and the solution was incubated overnight (20 hrs) in the dark at room temperature.

After incubation, the solution was centrifuged at 12,000 rpm for 5 minutes with the supernatant transferred into another 1.5 ml eppendorf tube. 200 µL supernatant was added into an amber autovial which had a 300 µL inlet, fix the top with a crimper for HPLC analysis.

Solvents and separation conditions were as described (Fariss. Jones). Levels of GSH and GSSG were quantified relative to authentic standards. Gamma-glutamyl-glutanmate was used as an internal standard to assess derivatization efficiency.

Comparison of values for clinical chemistry, hematology and body weights vs baseline were analyzed by way of paired t-test on SAS for Windows with significance set at $P<0.05$. Means of values at each measured time point were separated by a one-way ANOVA with significance set at $P<0.05$. The difference in GSH:GSSG between day 84 and baseline were analyzed between groups by way of SAS for Windows in a one-way ANOVA with significance set at $P<0.05$.

Results

Concentrations of lipoic acid (ppm) in food as determined over 7 successive assays (0, 28, 56, 84, 112, 140, 168 days) were within the range of expected assay sensitivity and production parameters typically encountered at our facility (Table 2).

The food intake data were unremarkable. Most animals in all groups ingested more food at 6 months, on average, than at the beginning of the study. Body weight data were unremarkable except that some weight loss occurred initially in the 4,500 ppm inclusion group but that change appeared to reverse by 6 months time. Body condition scores did not appear to be affected by this minor loss of weight.

The routine physical examinations did not reveal any evidence of nutrition related abnormalities or DL-alpha-lipoic acid toxicity. All animals in the study population remained normal during the entire course of the study. Occasional vomiting was observed in several animals during the course of the study; however, a trend was not observed that would lead one to the conclusion that the vomiting may be attributable to lipoic acid. One animal, in the highest inclusion group, was dropped from the study at day 21 for weight loss and leukocytosis. The leukocytosis in this animal had not resolved by the end of the study and is suspected to be attributable to some other disease process.

When serum biochemistry values for days 28, 56, 84, 112, 140, and 168 were compared with the initial values for the same group of dogs, several statistical differences were noted, however, none of these were considered biologically significant because these values were within or very near the laboratory reference range and consistent trends over months were noted. Comparisons between the controls and the other treatment groups at each time period also revealed several statistical differences, however, none of these were considered biologically significant because these values were within or very near the clinical laboratory reference ranges and no trends were present.

When the hematology values for days 28, 56, 84, 112, 140 and 168 were compared with the initial values for the same group of dogs, several statistical differences were noted; however, none of these were considered biologically significant because these values were within or very near the laboratory reference range and no trends were present. Comparison between the controls and the other treatment groups at each time period revealed several statistical differences: however, none of these were considered biologically significant because these values were within or very near the clinical laboratory reference ranges and no trends were present.

GSH:GSSG Ratio

The change in GSH:GSSG ratio over 84 days of feeding displayed a significant overall effect of diet ($P=0.024$) with all supplemented groups having an increase in the ratio (Table 3). ANOVA revealed a significant difference, compared to the basal food, for the lowest and highest inclusions, however, the largest numerical increase was in the lowest inclusion level. That is to say, the changes in the GSH:GSSG ratio for the highest and lowest inclusion were significantly different from the change observed over this same time period in the basal food. Ratios for 4 points could not be determined at day 84 as no GSSG was detectable in any of these samples (1 control, 3 treatment groups). As such, the values for supplemented groups may have displayed even higher ratios of GSH:GSSG if the assay had been sensitive enough to detect the low levels of GSSG at day 84.

TABLE 2

| Inclusion Rate Standard Percent (ppm) | Average | Standard Deviation | Target |
|---|---|---|---|
| 0 | 24 | 17 | N/A |
| 150 | 151 | 13 | 101 |
| 1,500 | 1471 | 113 | 98 |
| 3,000 | 2869 | 250 | 96 |
| 4,500 | 4176 | 642 | 93 |

TABLE 3

Change In Mean Ratio Of GSH:GSSG From Day 0 To Day 84 In Dogs Consuming DL-Alpha Lipoic Acid In An Extruded Food

| Inclusion | Difference in GSH:GSSG ratio - day 0 to day 84 Inclusion compared to baseline food | N | P value |
|---|---|---|---|
| 0 ppm | −9.2 +/− 26 | 5* | NA |
| 150 ppm | 70 +/− 20 | 6 | 0.003 |
| 1,500 ppm | 24 +/− 7 | 6 | 0.16 |
| 3,000 ppm | 10 +/− 4 | 4* | 0.46 |
| 4,500 ppm | 50 +/− 36 | 4* | 0.03 |

*1 dog in the control and 4,500 ppm group had no detectable GSSG at day 84 while 2 dogs in the 3,000 ppm group had no detectable GSSG at day 84.

Further observations with respect to alpha-lipoic acid are applicable. Chronic feeding of alpha-lipoic acid in diet is safe and effective. It improves the reduced glutathione (GSH) to oxidized glutathione (GSSG) ratio. The chronic administration of alpha-lipoic acid in the diet can be for periods of one, two, three, four, five, or six months minimum up through a period of one, two, three, four, five years or even more including the lifetime of the animal. The alpha-lipoic acid functions without any special protection in the diet such as encapsulation and need not be present in the diet in a unit dosage form such as those used in pharmaceuticals, for example, tablet, pill, capsule and the like. The lipoic acid is provided in the diet in a minimum of about 25, 50, 75, or 100 ppm of diet. The uppermost range is just below its toxic level, all the way down to about 400, 300, or 200 ppm of diet. Generally, one does not go beyond about 6 or 7 mg/kg body weight of animal per day, more generally not above about 5. The alpha-lipoic acid improves antioxidant defense capabilities as well as improves the animal's ability to resist oxidative damage. All this is done with the proper quantities of other antioxidants present such as vitamin E and vitamin C. This demonstrates that the action of alpha-lipoic acid is beyond that of vitamin C and/or vitamin E.

Example 3

Experimental Conditions

Twenty dogs were fed for 30 days. Ten were fed an AAFCO level control food and 10 other dogs were fed the AAFCO level control food containing 150 ppm alpha-lipoic acid. At the end of the end of the 30 days whole blood samples were collected from each dog in Paxgene tubes.

Total RNAs were isolated from whole blood samples using the PAXgene RNA isolation kit. All measurements were done with the canine 2 Affymetrix genechips. For statistical analysis, all measurements were normalized with RMA. All analysis was performed using Partek. An ANOVA t-test was performed for genes that are differentially expressed between the control and test foods, (at least a 20% change in expression with a pvalue<0.05)

Differentially expressed genes were analyzed with the GeneGo pathway analysis software. Dogs fed lipoic acid for 30 days exhibited an interferon mediated antiviral response. Genes up-regulated by feeding dogs lipoic acid for 30 days that are involved in interferon mediated antiviral response are listed in Table 4.

TABLE 4

| | | | 30-days lipoic acid canine adult | |
|---|---|---|---|---|
| Gene Symbol | Protein | Protein Name | Fold Up-regulated | p-value |
| CREBBP | CBP Human | CREB-binding protein | 1.2 | 0.04 |
| EIF2AK2 | E2AK2 Human | Interferon-induced double stranded RNA-activated protein | 1.4 | 0.04 |
| IFNAR2 | INAR2 Human | interferon-alpha/beta receptor beta chain precursor | 1.3 | 0.01 |
| IFNGR2 | INGR2 Human | interferon-gamma receptor beta chain precursor | 1.2 | 0.03 |
| IRF9 | IRF9 Human | interferon regulatory factor 9 | 1.3 | 0.2 |
| JAK2 | JAK2 Human | Tyrosine protein kinase JAK2 | 1.4 | 0.01 |
| RNASEL | RN5A Human | 2-5A-dependent ribonuclease | 1.5 | 0.04 |

Based on the studies of dogs fed lipoic acid for 30 days, the inventors have surprisingly found that cell surface receptors for interferon alpha/beta and interferon gamma are increased leading to the potential for increasing the entire interferon mediated antiviral defense mechanism. The inventors have found that JAK2, a key activator of STAT1 and STAT2, is up regulated. Interferon regulatory factor 9 (IFR9) is up-regulated. IFR9, STAT1 and STAT2 form a complex (ISFG3) that translocates to the nucleus and up regulates the antiviral genes, interferon-induced, double stranded RNA-activated protein kinase (PKR) and 2-5A-dependent ribonuclease (RnaseL). PKR inhibits elF2S1 via phosphorylation leading to an inhibition of viral protein synthesis. RnaseL cleaves viral RNA inhibiting viral replication and function.

The invention is not to be limited in scope by the specific embodiments disclosed in the examples, which are intended as illustrations of a few aspects of the invention, and any embodiments, which are functionally equivalent, are within the scope of this invention. Indeed, various modifications of the invention in addition to those shown and described herein will become apparent to those skilled in the art and are intended to fall within the appended claims.

For any references that have been cited, the entire disclosures of which are incorporated herein by reference.

What is claimed is:

1. A pet food composition comprising an effective amount of lipoic acid to enhance antiviral activity in a companion animal, wherein said effective amount of lipoic acid to enhance antiviral activity in a companion animal is at least 25 ppm to about 600 ppm, wherein the composition further comprises a source of protein and a source of fat, and wherein the pet food meets the ordinary nutritional requirements of an adult pet.

2. The composition of claim 1, wherein the effective amount is at least about 50 ppm.

3. The composition of claim 1, wherein the effective amount is at least about 100 ppm.

4. The composition of claim 1, wherein the effective amount is about 100 ppm to about 200 ppm.

5. The composition of claim 1, wherein the companion animal is a dog.

6. The composition of claim 1, wherein the companion animal is a cat.

7. The composition of claim 1, wherein the effective amount is effective to enhance innate antiviral activity in a companion animal.

* * * * *